United States Patent

Rolfs et al.

[11] Patent Number: 5,414,082
[45] Date of Patent: May 9, 1995

[54] METHOD FOR PRODUCING 1-UNSUBSTITUTED 3-AMINOPYRROLES

[75] Inventors: Andreas Rolfs; Jürger Liebscher, both of Berlin; Klaus Unverferth, Dresden; Gottfried Faust, Radebeul, all of Germany

[73] Assignee: Arzneimittelwerk Dresden GmbH, Radebeul, Germany

[21] Appl. No.: 104,795

[22] Filed: Aug. 11, 1993

[30] Foreign Application Priority Data

Aug. 20, 1992 [DE] Germany .................. 42 27 479.6

[51] Int. Cl.$^6$ ........................................... C07D 207/34
[52] U.S. Cl. ...................................... 544/60; 544/141; 544/372; 546/208; 546/281; 548/532; 548/557
[58] Field of Search ............... 546/281, 208; 544/141, 544/60, 372; 548/532, 557

[56] References Cited

U.S. PATENT DOCUMENTS 4,198,502  4/1980  Tarzia et al. ..................... 542/414

FOREIGN PATENT DOCUMENTS 0431371  6/1991  European Pat. Off. .
2605419  1/1977  Germany .

OTHER PUBLICATIONS

Knoll et al, Russian Article (Khimia Geterociklich) (1985) No. 5, p. 628.
Bird & Cheeseman editors: Comprehensive Heterocyclic Chem., vol. 4, Part 3, Pergaon Press (1984).
S Rajappa et al., Nitroenamines, Part IV., Indian Jnal. Chem. vol. 16b, (Oct. 1977), p. 886.

*Primary Examiner*—Mukund J. Shah
*Assistant Examiner*—Matthew V. Grumbling
*Attorney, Agent, or Firm*—Schweitzer Cornman & Gross

[57] ABSTRACT

A process for producing pharmacologically active 1-unsubstituted 3-aminopyrroles of the formula

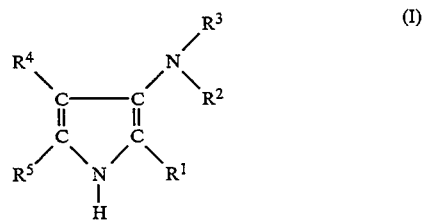

by ring transformation of a corresponding 1,2-thiazolium pyrrole in a single step, without producing harmful byproducts.

4 Claims, No Drawings

METHOD FOR PRODUCING 1-UNSUBSTITUTED 3-AMINOPYRROLES

FIELD OF THE INVENTION

The invention relates to a process for producing 1-unsubstituted 3-aminopyrroles which are valuable drugs with activity on the central nervous system, having particularly anticonvulsive properties.

BACKGROUND OF THE INVENTION 3-morpholino-pyrrole-2-carboxylic acid esters can be produced from 3-aminothio acrylic acid amides and glycineesters as described by Knoll-, and J. Liebscher, in Khim. Geterotsikl. Soedin. 1985, p. 628. It is also known from European patent publication 431,371 to produce 3-aminopyrroles by various methods from precursors with open chains, having properties affecting the central nervous system. Furthermore, 4-sub-stituted-3-aminopyrroles are known as substances that are active on the central nervous system when the substituent is aminocarbonyl, as disclosed in German patent No. 2,605,419, or carbonyl groups, as disclosed in U.S. Pat. No. 4,198,502. All of these known processes have the disadvantage that either they require several steps, or produce harmful byproducts, such as alkylmercaptanes. N-substituted 1,2-thiazolium salts are known from C. W. Bird and G. W. H. Cheeseman, Comprehensive Heterocyclic Chemistry (Pergamon Press, Oxford, New York, Toronto, Sydney, Paris, Frankfurt, 1984, Vol. 4, S. 144) to enter in the ring transformation reactions to form thiophenes. Finally, it is know from S. Rajappa et al., Indian J. Chem. B, 15, 1977, p. 848 that 1,2-thiazolium salts in the presence of basis easily split off the substituents in the 2-position.

DETAILED DESCRIPTION OF THE INVENTION

The objective of the invention is to provide a new process for producing pharmacologically active 1-unsubstituted 3-aminopyrroles in a single step, without producing harmful byproducts.

The process of the present invention is a new synthesis for the pyrrole structure by which this heterocyclic moiety is created by the ring transformation of a corresponding 1,2-thazolium salt. This ring transformation also enables the forming of pyrroles which could not be produced with the heretofore known processes. The yields are high and the products can be simply purified mostly by single recrystalization.

In accordance with the foregoing objective 1-unsubstituted 3-aminopyrroles are produced of Formula I

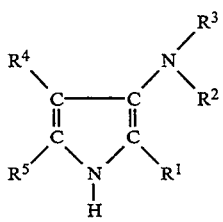

wherein
R¹ is hydrogen, alkyl, alkenyl, aryl, heteroaryl, nitro, cyano, acyl, alkoxycarbonyl, aminocarbonyl, aryloxycarbonyl, or a sulfonyl residue;
R² and R³ can be the same or different, namely hydrogen, aryl, or alkyl residue which can be substituted by hetero atoms, or R² and R³ can form together an alkyl bridge which can contain or be substituted with hetero atoms such as nitrogen, oxygen or sulfur;
R⁴ and R⁵ can be the same or different, namely hydrogen, alkoxycarbonyl, aminocarbonyl, or aminothiocarbonyl residue, or substituted or unsubstituted alkyl, aryl, heteroaryl residue,
by a ring transformation, suitably in the presence of a base, of a corresponding 1,2-thiazolium salt of Formula II

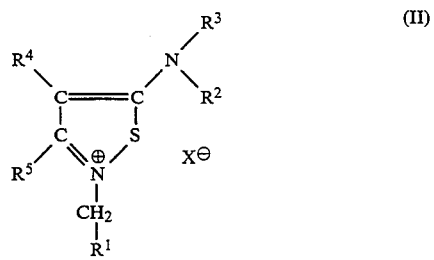

wherein the group R¹, and R², R³, and respectively R²/R³, R⁴, and R⁵ have the aforementioned meaning, and wherein X⁻ can be an acid residue, optionally a halogenide, perchlorate, tetrafluoroborate, hydrogen sulfate, sulfate, hydroxide, or triflate.

There was surprisingly no formation of 2-unsubstituted compounds of the 1,2-thiazolium salts of Formula II.

Suitably a tertiary amine, a basic N-heteroaromatic compound, an alkali hydride, an alkylamide, an alkali carbonate, an alkali hydroxide, or an ion exchange material can be employed as the base. The method of the invention enables the synthesis of 1-unsubstituted 3-aminopyrroles of Formula I in a single step reaction without the formation of harmful byproducts, such as hydrogen sulfide, or mercaptanes. The resulting compounds have a high anticonvulsive activity.

The 1,2-thiaxolium pyrrole starting materials of Formula II can be suitably prepared by the oxidation of corresponding aminovinylthiocarbonyl compounds.

The following illustrative specific procedure exemplifies the preparation of the 1,2-thiazolium pyrrole starting intermediates of Formula II. 10 mmol of a 3-alkoxycarbonyldimethylamino-2-arylthioacryl acid amid is dissolved in from about 80 to about 100 ml chloroform or ethanol. Then the solution is reacted with 10 mmol triethylamine, and then oxidized with bromine in chloroform over ice/water or during cooling while dropwise adding about 10 mmol bromine. After complete oxidation the reaction mixture is cooled over ice/water and rapidly extracted 2-3 times with chloroform. The various chloroform phases are washed with water and are concentrated on a rotating evaporator at a bath temperature <40° C. The residue is dissolved in a small amount of chloroform, acetone, or methanol, and the crystalline precipitate is formed with diethylether, as shown in the following table. The yield of the 1,2-isothiazolium pyrrole of Formula II is between about 50 and about 70%. If upon the adding of the diethylether a thick oil if formed, it can be directly employed after the removal of the solvent. In that case the yield is over 90%.

The starting materials for the preparation of the intermediates, is described, for example, by J. Liebscher et al., Z. Chem. vol. 27, p.8 (1987).

The following table illustrates the preparation of seven (i-vii) different 1,2-isothiazolium pyrroles of Formula II, wherein DEE designates diethylether.

| No. | $R^1$ | $-NR^2R^3$ | $R^4$ | $R^5$ | X | Elementary Formula | Decomposition (°C.) |
|---|---|---|---|---|---|---|---|
| (i) | $-COOCH_3$ | morpholino ($-N\underset{\smile}{\frown}O$) | phenyl | $-H$ | $HSO_4^-$ | $C_{16}H_{20}N_2O_7S_2$ 418.47 | 165 (decomp.) ($CH_3OH$/DEE) |
| (ii) | $-COOCH_3$ | $-NHC_6H_5$ | phenyl | $-CH_3$ | $Br^-$ | $C_{19}H_{19}N_2O_2SBr$ 419.32 | 172 (decomp.) ($CH_3OH$/DEE) |
| (iii) | $-COOC_2H_5$ | morpholino | 4-F-phenyl | $-H$ | $Br^-$ | $C_{17}H_{20}N_2O_3SFBr$ 431.30 | 130 (decomp.) ($CH_3OH$) |
| (iv) | $-COOCH_3$ | morpholino | 4-Cl-phenyl | $-H$ | $ClO_4^-$ | $C_{16}H_{18}N_2O_7SCl_2$ 453.28 | 79–80 (decomp.) (Aceton/DEE) |
| (v) | $-COOCH_3$ | morpholino | 4-Cl-phenyl | $-H$ | $Br^-$ | $C_{16}H_{18}N_2O_3SClBr$ 433.73 | 146 (decomp.) ($CH_3OH$/DEE) |
| (vi) | $-COO\text{-}i\text{-}C_4H_9$ | morpholino | 4-Cl-phenyl | $-H$ | $Br^-$ | $C_{19}H_{24}N_2O_3SClBr$ 475.81 | 140 (decomp.) ($CHCl_3$/DEE) |
| (vii) | $-COOCH_3$ | morpholino | 2-CH$_3$-phenyl | $-H$ | $Br^-$ | $C_{17}H_{21}N_2O_3SBr$ 413.31 | 156 (decomp.) ($CHCl_3$/DEE) |

EXAMPLES 1–18

In these examples the preparation of the following 1-unsubstituted 3-aminopyrroles is described:

4-phenyl-3-(morpholino-4-yl)pyrrole-2-carboxylic acid methylester,
4-(4-chlorophenyl)-3-(morpholino-4-yl)pyrrole-2-carboxylic acid methylester,
4-(4-chlorophenyl)-3-(morpholino-4-yl)pyrrole-2-carboxylic acid isobutyl ester,
4-(4-chlorophenyl)-3-(morpholino-4-yl)pyrrole-2-carboxylic acid butyl ester,
4-(4-bromophenyl)-3-(morpholino-4-yl)pyrrole-2-carboxylic acid ethyl ester,
4-(4-fluorophenyl)-3-(morpholino-4-yl)pyrrole-2-carboxylic acid ethyl ester,
4-(4-chlorophenyl)-3-(4-methylpiperazino-1-yl)pyrrole-2-carboxylic acid methylester,
4-(4-chlorophenyl)-3-(4-methylpiperazino-l-yl)pyrrole-2-carboxylic acid ethyl ester,
4-(4-chlorophenyl-3-(thiomorpholino-4-yl)pyrrole-2-carboxylic acid methylester,
4-(4-chlorophenyl)-3-amino-pyrrole-2-carboxylic acid ethyl ester,
4-(4-chlorophenyl)-3-benzylamino-pyrrole-2-carboxylic acid ethyl ester,
4-(pyridino-4-yl)-3-(morpholino-4-yl)pyrrole-2-carboxylic acid methylester,
4-(4-chlorophenyl )-3-(4-ethoxycarbethoxypiperidino-1-yl)pyrrole-2-carboxylic acid methylester,
4-(4-chlorophenyl)-3-(2-dimethylaminoethyl-1-methylamino)pyrrole-2-carboxylic acid methylester,
4-phenyl-3-phenylamino-5-methyl-pyrrole-2-carboxylic acid methylester,
2-cyano-4-phenylamino-5-methyl pyrrole,
4-ethoxycarbethoxy-3-phenylamino-pyrrole-2-carboxylic acid methylester, and
4-(4-chlorophenyl)-3-(morpholino-4-yl)-2-benzoyl pyrrole.

As shown in the following table, the aforementioned compounds were produced by dissolving 0.01 mole of the corresponding 1,2-thiazolium salt corresponding to the structure of Formula II, in 40–50 ml ethanol, methanol, acetonitrile, or chloroform, and then reacting with a small excess of a tertiary amine, a N-heteroaromatic compound, alkali hydroxide, or alkali carbonate, and heated for up to five minutes under reflux. The largest part of the evolving sulfur separated during the heating and this was filtered off. The mother liquor was cooled to 0° C. After about 2–3 hours the precipitated crystals of the 3-aminopyrrole of Formula I was filtered off by suction and recrystallized from the corresponding solvent. The yield can be increased in a manner known per se over the values given in Table I, by concentration of the mother liquor, reprecipitation with water, or a purification of the mother liquor in a chromatographic column.

When the 1,2-thiazolium salts were reacted with an alkali hydride, then dimethyformamide, dioxane, or tetrahydrofurane were used as a solvent. Processing took place in this case by pouring the reaction mixture onto ice water, filtration and subsequent recrystallization.

$F_p$ (°C.) designates the melting point of a compound.

| Example No. | $R^1$ | $-NR^2R^3$ | $R^4$ | $R^5$ | Elementary Formula MG (g/mol) | Recryst. $F_p$ (°C.) | Yield % |
|---|---|---|---|---|---|---|---|
| 1 | $-COOCH_3$ | morpholino (−N(CH₂CH₂)₂O) | phenyl | −H | $C_{16}H_{18}N_2O_3$ 286,32 | 179–181 ($CH_3OH$) | 81,4 |
| 2 | $-COOCH_3$ | morpholino | 4-Cl-phenyl | −H | $C_{16}H_{17}N_2O_3Cl$ 320,76 | 191–193 ($CH_3OH$) | 77,6 |
| 3 | $-COOC_4H_9(i)$ | morpholino | 4-Cl-phenyl | −H | $C_{19}H_{23}N_2O_3Cl$ 362,84 | 212–214 ($i$-$C_4H_9OH$) | 75,1 |
| 4 | $-COOC_4H_9$ | morpholino | 4-Cl-phenyl | −H | $C_{19}H_{23}N_2O_3Cl$ 362,84 | 161–163,5 ($CH_3OH$) | 63,0 |
| 5 | $-COOC_2H_5$ | morpholino | 4-Br-phenyl | −H | $C_{17}H_{19}N_2O_3Br$ 379,24 | 189–192 ($C_2H_5OH$) | 82,0 |
| 6 | $-COOC_2H_5$ | morpholino | 4-F-phenyl | −H | $C_{17}H_{19}N_2O_3F$ 318,34 | 183,5–185 ($C_2H_5OH$) | 81,4 |
| 7 | $-COOCH_3$ | 4-methylpiperazino (−N(CH₂CH₂)₂N−CH₃) | 4-Cl-phenyl | −H | $C_{17}H_{20}N_3O_2Cl$ 333,81 | 207–209 ($CH_3OH$) | 68,3 |
| 8 | $-COOC_2H_5$ | 4-methylpiperazino | 4-Cl-phenyl | −H | $C_{18}H_{22}N_3O_2Cl$ 347,83 | 239–241 ($C_2H_5OH$) | 81,3 |
| 9 | $-COOCH_3$ | thiomorpholino (−N(CH₂CH₂)₂S) | 4-Cl-phenyl | −H | $C_{16}H_{17}N_2O_2SCl$ 336,82 | 194,5–196 ($CH_3OH$) | 72,8 |
| 10 | $-COOC_2H_5$ | $-NH_2$ | 4-Cl-phenyl | −H | $C_{13}H_{13}N_2O_2Cl$ 264,70 | 99–100 ($C_6H_{12}$) | 40,7 |
| 11 | $-COOC_2H_5$ | $-NHCH_2$-phenyl | 4-Cl-phenyl | −H | $C_{20}H_{19}N_2O_2Cl$ 354,82 | 111–112 ($C_2H_5OH$) | 83,6 |

-continued

| Example No. | R¹ | —NR²R³ | R⁴ | R⁵ | Elementary Formula MG (g/mol) | Recryst. $F_p$ (°C.) | Yield % |
|---|---|---|---|---|---|---|---|
| 12 | —COOCH₃ | morpholino (—N(CH₂CH₂)₂O) | 4-methylpyridin-2-yl | —H | $C_{15}H_{17}N_3O_3$ 287,31 | 252 (Zers.) (CH₃OH) | 69,5 |
| 13 | —COOCH₃ | —N(CH₂CH₂)₂CH—COC₂H₅ (piperidine with COC₂H₅) | 4-chlorophenyl | —H | $C_{20}H_{23}N_2O_4Cl$ 390,85 | 145–146 (C₂H₅OH) | 73,8 |
| 14 | —COOCH₃ | —N(CH₂)₂N(CH₃)₂ with CH₃ | 4-chlorophenyl | —H | $C_{17}H_{22}N_3O_2Cl$ 335,82 | 138 (C₂H₅OH) | 91,2 |
| 15 | —COOCH₃ | —NH—phenyl | 2-methylphenyl | —CH₃ | $C_{19}H_{18}N_2O_2$ 306,35 | 163–65 (CH₃OH) | 99,0 |
| 16 | —CN | —NH—phenyl | 2-methylphenyl | —CH₃ | $C_{18}H_{15}N_3$ 273,33 | 189–190 (CHCl₃) | 82,1 |
| 17 | —COOCH₃ | —NH—phenyl | —COOC₂H₅ | —CH₃ | $C_{16}H_{18}N_2O_4$ 302,32 | 162–163 (C₂H₅OH) | 96,5 |
| 18 | —CO—phenyl | morpholino (—N(CH₂CH₂)₂O) | 4-chlorophenyl | —H | $C_{21}H_{19}N_2O_2Cl$ 366,83 | 207–208 (C₆H₆) | 66,0 |

The anticonvulsive efficacy was tested of some 1-unsubstituted 3-aminopyrroles of Formula I. More particularly, the ability of some compounds was determined to inhibit cramps in mice which manifested maximum occurrence of the cramps under electric excitation.

100% inhibition of cramps was observed with a dose of $1 \times 10^{-3}$ mol/kg body weight of intraperitonially administered 3-(morpholino-4-yl)-4-phenyl-pyrrole-2-carboxylic acid methylester.

An 80% inhibition of cramps was observed upon the intraperitonial administration of $5 \times 10^{-4}$ mol/kg body weight of 4-(4-chlorophenyl)-3-(thiomorpholino-4-yl)pyrrole-2-carboxylic acid methylester.

The elementary analyses are provided in the format of calculated data/actual data.

The following examples describe some specific suitable process variants for preparing the 1-unsubstituted 3-aminopyrroles in accordance with the present invention.

EXAMPLE 19

4-(4-chlorophenyl)-3morpholino-1-yl)pyrrole-2-carboxylic acid-N-butylester 0.01 mole of 4-(4-chlorophenyl)-5-(morpholino-4-yl)-N-butyloxycarbonyl-methyl-1,2-thiazolium bromide is dissolved in 50 ml ethanol, and 0.012 mol triethylamine dissolved in 5 ml ethanol is added dropwise. The solution is brought to boil while stirring. The precipitating sulfur is filtered off while hot, and the mother liquor is reacted with 10 ml hot water. The solution is cooled to 0° C. and the precipitated crystals are sucked off. The additional sulfur is removed during dissolution in methylene chloride. The methylene chloride solution is concentrated to dryness and dissolved in methanol. The precipitating crystals are sucked off and are dried.

The yield is 63% of the theoretical, yielding 2.28 g of a material, the elementary analysis of which is C: 62.89/62.62; H: 6.39/6.44; N: 7.72/7.80; Cl: 9.77/9.78.

EXAMPLE 20

4-(4-chlorophenyl)-3-(4-methylpiperazino-1-yl)pyrrole-2-carboxylic acid methylester 0.01 mol of 4-(4-chlorophenyl)-5-(4-methylpiperazino-1-yl)-N-methoxycarbonyl-methyl-1,2-thiazoliumhydroxide is heated in 50 ml methanol for 5 minutes under reflux. The solution is cooled to 0° C. and after 2 hours the precipitated crystals are sucked off and recrystallized from methanol.

68% of theoretical yield of 2.27 g of material was obtained, having an elementary analysis of C: 61.16/61.39; H: 6.04/5.90; N: 12.59/12.49; Cl: 10.62/10.61.

EXAMPLE 21

3-(morpholino-4-yl)-4-(pyridino-4-yl)pyrrole-2-carboxylic acid methylester 0.01 mol of 5-morpholino-4-yl)-4-(pyridino-4-yl)-N-methoxycarbonylmethyl-1,2-thiazoliumiodide is heated in a 1 n - ethanolic sodium hydroxide solution for 2 minutes. The solution is cooled, precipitated crystals are sucked off and then purified in a chromatographic column from the attached sulfur.

The yield is 69.5% of theoretical and was 2 g, having an elemental analysis of C: 62.70/62.89; H: 5.96/6.00; N: 14.63/14.67.

EXAMPLE 22

3-benzylamino-4-(4-chlorphenyl)pyrrole-2-carboxylic acid ethyl ester 0.01 mol of 5-benzylamino-4-(4-chlorophenyl)-N-ethoxycarbonylmethyl-1,2-thiazoliumbromide is boiled in 40 ml of an aqueous-ethanolic 0.01 n potassium carbonate solution for 5 minutes. After cooling to 0° C., the crystals are sucked off and recrystallized from ethanol. A yield of 83.6% of theoretical of 2.97 g material was recovered, having an elemental analysis of C: 67.69/67.54; H: 5.40/5.38; N:7.90/8.00; Cl: 9.99/10.13.

We claim:

1. A process for producing a 1-unsubstituted 3-aminopyrrole of Formula (I)

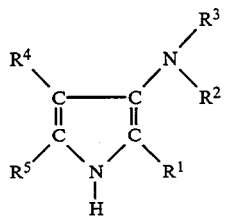

wherein $R^1$ is hydrogen, alkyl, alkenyl, aryl, heteroaryl, nitro, cyano, acyl, alkoxycarbonyl, amino, carbonyl, aryloxycarbonyl, or a sulfonyl residue;

$R^2$ and $R^3$ can be the same or different, hydrogen, aryl, or alkyl residue which are optionally substituted by hetero atoms, or $R^2$ and $R^3$ can form together an alkyl bridge which optionally contains or is optionally substituted with a hetero atom optionally containing nitrogen, oxygen, or sulfur; and $R^4$ and $R^5$ can be the same or different, hydrogen, alkoxycarbonyl, aminocarbonyl, aminothiocarbonyl, substituted or unsubstituted alkyl, aryl, or heteroaryl residue, by transforming the ring, optionally in the presence of a base, of a corresponding 1,2-thiazolium salt of Formula (II)

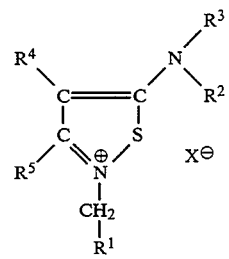

wherein $R^1$, and $R^2$, $R^3$, and respectively $R^2/R^3$, $R^4$, and $R^5$ have the aforementioned meanings, and wherein $X^-$ is an acid residue.

2. The process of claim 1, wherein the compound of Formula I is:
   4-phenyl-3-(morpholino-4-yl)pyrrole-2-carboxylic acid methylester,
   4-(4-chlorophenyl)-3-(morpholino-4-yl)pyrrole-2-carboxylic acid methylester,
   4-(4-chlorophenyl)-3-(morpholino-4-yl)pyrrole-2-carboxylic acid isobutyl ester,
   4-(4-chlorophenyl)-3-(morpholino-4-yl)pyrrole-2-carboxylic acid butyl ester,
   4-(4-bromophenyl)-3-(morpholino-4-yl)pyrrole-2-carboxylic acid ethyl ester,
   4-(4-fluorophenyl)-3-(morpholino-4-yl)pyrrole-2-carboxylic acid ethyl ester,
   4-(4-chlorophenyl)-3-( 4-methylpiperazino- 1-yl)pyrrole-2-carboxylic acid methylester,
   4-(4-chlorophenyl)-3-(4-methylpiperazino-1-yl)pyrrole-2-carboxylic acid ethyl ester,
   4-(4-chlorophenyl-3-(thiomorpholino-4-yl)pyrrole-2-carboxylic acid methylester,
   4-(4-chlorophenyl)-3-amino-pyrrole-2-carboxylic acid ethyl ester,
   4-(4-chlorophenyl)-3-benzylamino-pyrrole-2-carboxylic acid ethyl ester,
   4-(pyridino-4-yl)-3-(morpholino-4-yl)pyrrole-2-carboxylic acid methylester,
   4-(4-chlorophenyl )-3-( 4-ethoxycarbonylpiperidino-1-yl )-2-carboxylic acid methylester,
   4-(4-chlorophenyl)-3-pyrrole-2-carboxylic acid methylester,
   4-phenyl-3-phenylamino-5-methyl pyrrole-2-carboxylic acid methylester,
   2-cyano-4-phenyl-3-phenylamino-5-methyl pyrrole,
   4-ethoxycarbonyl-5-methyl-3-phenylamino-pyrrole-2-carboxylic acid methylester, and
   (4-chlorophenyl)-3-(morpholino-4-yl)-2-benzoyl pyrrole.

3. The process of claim 1, wherein the base is a tertiary amine, a basic N-heteroaromatic compound, an alkali hydride, an alkylamide, an alkali carbonate, an alkali hydroxide, or an ion exchanger.

4. The process of claim 1, wherein said acid residue is one of halogenide, perchlorate, tetrafluoroborate, hydrogen sulfate, sulfate, or triflate.

* * * * *